US012382962B2

(12) United States Patent
Celerier et al.

(10) Patent No.: US 12,382,962 B2
(45) Date of Patent: Aug. 12, 2025

(54) BIOLOGICALLY ACTIVE SUBSTANCE, METHOD FOR MANUFACTURING SAME AND USE THEREOF AS AN AGENT FOR PROTECTING A BIOLOGICAL TISSUE

(71) Applicant: UNIVERSITE DE LIMOGES, Limoges (FR)

(72) Inventors: Julien Celerier, Limoges (FR); Charlotte Moine, Limoges (FR); Céline Faugeron-Girard, Saint Just le Martel (FR); Vincent Gloaguen, Aixe sur Vienne (FR)

(73) Assignee: UNIVERSITE DE LIMOGES, Limoges (FR)

( * ) Notice: Subject to any disclaimer, the term of this patent is extended or adjusted under 35 U.S.C. 154(b) by 832 days.

(21) Appl. No.: 17/416,881

(22) PCT Filed: Dec. 20, 2019

(86) PCT No.: PCT/IB2019/061171
§ 371 (c)(1),
(2) Date: Jun. 21, 2021

(87) PCT Pub. No.: WO2020/128991
PCT Pub. Date: Jun. 25, 2020

(65) Prior Publication Data
US 2021/0337807 A1 Nov. 4, 2021

(30) Foreign Application Priority Data
Dec. 21, 2018 (FR) ...................................... 1874070

(51) Int. Cl.
*A61K 8/9728* (2017.01)
*A01N 65/00* (2009.01)
*A61Q 17/00* (2006.01)

(52) U.S. Cl.
CPC ............ *A01N 65/00* (2013.01); *A61K 8/9728* (2017.08); *A61Q 17/00* (2013.01); *A61K 2800/84* (2013.01)

(58) Field of Classification Search
CPC ................................ A61K 8/9728; A61Q 17/00
See application file for complete search history.

(56) References Cited

U.S. PATENT DOCUMENTS

| 4,769,363 A | * | 9/1988 | Misaki ................ C08B 37/0024 514/23 |
| 6,387,847 B1 | * | 5/2002 | Yvin ...................... A01N 43/16 504/117 |
| 2007/0207098 A1 | | 9/2007 | Nawamura et al. |
| 2009/0208525 A1 | | 8/2009 | Nawamura et al. |
| 2009/0226388 A1 | | 9/2009 | Nawamura et al. |
| 2013/0195911 A1 | | 8/2013 | Baier et al. |
| 2019/0254288 A1 | | 8/2019 | Faugeron et al. |

FOREIGN PATENT DOCUMENTS

| CN | 1078094 A | 11/1993 |
| CN | 1345540 A | 4/2002 |
| CN | 107913203 A | 4/2018 |
| EP | 1 690 914 A1 | 8/2006 |
| FR | 2 766 059 A1 | 1/1999 |
| KR | 10-2011-0088907 A | 8/2011 |
| KR | 10-2011-0088915 A | 8/2011 |
| KR | 10-2012-0131065 A | 12/2012 |
| KR | 10-2014-0081982 A | 7/2014 |
| KR | 10-2016-0097854 A | 8/2016 |
| KR | 20170039935 A * | 10/2017 |
| WO | 98/49331 A1 | 11/1998 |
| WO | 2011/099665 A1 | 8/2011 |
| WO | 2011/112179 A1 | 9/2011 |
| WO | 2018/069497 A1 | 4/2018 |

OTHER PUBLICATIONS

Synytsya et. al. (Glucans from fruit bodies of cultivated mushrooms Pleurotus ostreatus and Pleurotus eryngii: Structure and potential prebiotic activity, Carbohydrate Polymers, vol. 76, Iss 4, May 16, 2009, pp. 549-556), retrieved from internet on Apr. 10, 2024. (Year: 2009).*
KR20170039935A translated doc (Year: 2017).*
Ng Tzi Bun; "Mushroom proteins related to host defense"; International Journal of Medicinal Mushrooms; 2005; pp. 221-236; vol. 7; Issue 1 Begell, Biosis, Biosciences Information Service, Philadelphia, PA, US; XP002769700; Publication Date Jan. 1, 2005; DOI: 10.1615/INTJMEDMUSHR.V7.112.210.
Thomson Scientific, London, GB; vol. 2011; No. 57; An 2011-K73906; Retrieved from Database WPI; XP002794700.
Li et al.; "Purification, in vitroantioxidant and in vivo anti-aging activities of soluble polysaccharides by enzyme-assisted extraction from Agaricus bisporus"; International Journal of Biological Macromolecules; Elsevier BV, NL; vol. 109; XP085346851; Publication Date Dec. 21, 2017; DOI: 10.1016/J.IJBIOMAC.2017.12.108; ISSN:0141-8130; pp. 457-466.

(Continued)

*Primary Examiner* — Terry A McKelvey
*Assistant Examiner* — Jacob A Boeckelman
(74) *Attorney, Agent, or Firm* — NIXON & VANDERHYE

(57) ABSTRACT

The biologically active substance is obtained or capable of being obtained by alkaline extraction, using an aqueous solution of at least one base in the presence of at least one reducing agent, of at least one macroscopic edible mushroom reduced to powder, to obtain a mixture having a liquid portion containing the soluble extracted materials and a solid portion formed of insoluble solid particles; filtering the resulting mixture to remove the solid portion and optionally clarifying the liquid portion; neutralising the liquid portion using a cation exchange resin and optionally filtering/clarifying the liquid portion thus neutralised to obtain the biologically active substance in the aqueous phase; and treating the resulting aqueous phase, the treatment being selected from dilution in water, concentration, dehydration and lyophilisation to obtain a biologically active substance which is, respectively, more diluted in water, in an aqueous solution more concentrated, dehydrated in powder form or lyophilised.

12 Claims, 3 Drawing Sheets

(56) References Cited

OTHER PUBLICATIONS

International Search Report for PCT/IB2019/061171, dated Mar. 9, 2020.
Written Opinion of the International Search Authority for PCT/IB2019/061171, dated Mar. 9, 2020.

* cited by examiner

BIOLOGICALLY ACTIVE SUBSTANCE, METHOD FOR MANUFACTURING SAME AND USE THEREOF AS AN AGENT FOR PROTECTING A BIOLOGICAL TISSUE

This application is the U.S. national phase of International Application No. PCT/IB2019/061171 filed 20 Dec. 2019, which designated the U.S. and claims priority to FR Patent Application No. 1874070 filed 21 Dec. 2018, the entire contents of each of which are hereby incorporated by reference.

BACKGROUND OF THE INVENTION

Field of the Invention

The present invention relates to a biologically active substance obtained from at least one macroscopic edible mushroom, to the method of manufacturing same and to the use thereof as an agent for protecting a biological tissue.

Description of the Related Art

By biological tissue is meant an envelope of an organism, which constitutes a direct interface between the organism and the external environment and must therefore be protected from any attack by any exogenous agent.

As biological tissue, we can therefore mention both plant tissues, such as the aerial parts of plants, vines, wheat, fruits, tomatoes, potatoes, etc., and human or animal skin.

Plant tissues are susceptible to be attacked by pathogens, such as viruses, bacteria, fungi or insects, and may respond to these attacks by developing, particularly through the action of so-called elicitor/repairer compounds, physiological or metabolic natural defence responses which consist of:
  strengthening pre-existing cell barriers by stimulating the lignification of plant cell walls;
  the synthesis by the plant of compounds with antibiotic activity, such as phytoalexins;
  the synthesis of enzymatic proteins that can attack the wall of pathogens, such as chitinases or glucanases.

The human or animal skin is the direct interface between man and his environment. It must therefore protect against external attacks, but it also suffers damage related to this environment. This damage can be significant, such as wounds or burns, but also slower and "minor", such as wrinkles.

The mechanism for the appearance of wrinkles involves both intrinsic and extrinsic factors. Among the intrinsic factors inducing the formation of wrinkles, there are several mechanisms: a decrease in hydration; a decrease in the production of collagen III and a predominance of the more rigid type I collagen; a 50% decrease in cell renewal; and a rarefaction of keratinocytes due to a decrease in their capacity to migrate towards the surface of the epidermis.

In addition, the body has its own defence system to neutralise free radical damage, but as we age, the effectiveness of this system declines and our need for anti-oxidants increases.

In addition to this genetically programmed ageing, there are environmental factors that accelerate this process: climatic and pathological aggressions, etc. Behaviour can also have a major influence on the appearance of the skin: smoking, alcohol, etc. Dermatologists estimate that 90% of skin ageing is due to these exogenous factors.

In general, the skin repair process must involve several factors, such as proliferation of dermal and epidermal cells; synthesis and/or remodelling of the extracellular matrix; and protection against free radicals.

SUMMARY OF THE INVENTION

The present inventors have sought a biologically active substance advantageously of natural origin and easy to manufacture which can effectively protect any biological tissue, playing in particular the role of elicitors/repairers in the case of plant tissue, and the role of protective cosmetic ingredient in the case of skin.

Through this research, they discovered a biological substance from a macroscopic edible mushroom, which they demonstrated as having protective properties for all these biological tissues.

The subject-matter of the present invention is therefore firstly a biologically active substance obtained or capable of being obtained by:
  alkaline extraction, using an aqueous solution of at least one base in the presence of at least one reducing agent, of at least one macroscopic edible mushroom reduced to powder, to obtain a mixture having a liquid portion containing the soluble extracted materials and a solid portion formed of insoluble solid particles;
  filtering the resulting mixture to remove the solid portion and optionally clarifying the liquid portion;
  neutralising the liquid portion using at least one cation exchange resin and optionally filtering/clarifying the liquid portion thus neutralised to obtain the biologically active substance in the aqueous phase; and
  treating the resulting aqueous phase, the treatment being selected from dilution in water, concentration, dehydration and lyophilisation to obtain a biologically active substance which is, respectively, more diluted in water, in an aqueous solution that is more concentrated, dehydrated in powder form or lyophilised.

The mushroom(s) subjected to the extraction can be selected from the group formed by oyster mushrooms, parasol mushrooms and button mushrooms.

The base can be selected from hydroxylated bases, such as sodium hydroxide and potassium hydroxide; the reducing agent(s) can be selected from alkali borohydrides, such as sodium or potassium borohydride; and the cation exchange resin can be selected from resins with sulphonic, phosphorus, carboxymethyl, carboxylic groups.

The biologically active substance can comprise, per 100 parts by weight of dry matter:
  30 to 75 parts by weight of total sugars, of which:
    9 to 25 parts by weight of β-glucans; and
    0.8 to 2.4 parts by weight of glucosamine and/or acetylated glucosamine;
  7 to 36 parts by weight of total peptides/total proteins;
  the remainder being mineral matter,
80 to 100% of the organic compounds having, in particular, a mass, based on the average molecular size, of between 20 and 45 kDa.

The invention also relates to a process for the manufacturing of a biologically active substance, characterised by the fact that it comprises the following successive steps consisting in:
  (a) carrying out an alkaline extraction, by means of an aqueous solution of at least one base in the presence of at least one reducing agent, of at least one macroscopic edible mushroom reduced to powder, in order to obtain a mixture having a liquid portion containing the soluble extracted materials and a solid portion formed of insoluble solid particles;

(b) filtering the resulting mixture in order to remove the solid portion from it, optionally followed by clarification;

(c) neutralising the liquid portion with at least one cation exchange resin, optionally followed by a filtration/clarification of the liquid portion thus neutralised to obtain the biologically active substance in the aqueous phase; and (d) optionally, carrying out a further treatment of the resulting aqueous phase, selected from dilution in water, concentration, dehydration and lyophilisation to obtain a biologically active substance which is, respectively, more diluted in water, in an aqueous solution that is more concentrated, dehydrated in powder form or lyophilised.

The operation(s) in step (b) can result in the removal of solid particles larger than 1 μm.

Any filtration/clarification in step (c) aims to remove any cation exchange resin particles that may remain in the aqueous phase.

A mushroom selected from the group formed by oyster mushrooms, parasol mushrooms and button mushrooms can be used, the mushroom powder representing in particular 5 to 15% by weight of the aqueous solution of at least one base.

For the alkaline extraction, sodium hydroxide or potassium hydroxide can be used as the base, and an alkaline borohydride, such as sodium or potassium borohydride, as the reducing agent, the reducing agent(s) being used in particular in an amount of 0.05 to 1 g/100 mL of the aqueous solution of at least one base; and, for neutralisation, at least one ion exchange resin can be used, chosen from resins having sulphonic, phosphorus, carboxymethyl or carboxylic groups.

The alkaline extraction can be carried out by heating the aqueous solution of at least one base, in the presence of at least one reducing agent, to a temperature of 25 to 100° C. for at least 2 hours with stirring.

The invention also relates to the use of a biologically active substance as defined above or prepared by the process as defined above, as an agent for protecting a biological tissue against attack by at least one exogenous agent.

The biological tissue can be a plant tissue, the exogenous agent(s) can be pathogenic fungi, bacteria, viruses, insects and/or a physical attacking agent, such as rain, frost, temperature and environmental stresses, and the protective agent can be an elicitor/repairing agent for of said plant tissue, in particular for agronomically useful or ornamental plants, in particular for a preventive treatment against cryptogamic diseases and bacterial diseases, especially those selected from the group formed by fruit storage diseases, diseases of vines, fruit trees, vegetable crops and cereals. Examples of these cryptogamic and bacterial diseases are downy mildew (*Plasmopara viticola*);
powdery mildew (*Erysiphe necator*);
diseases caused by *Xanthomonas* sp. and *Pseudomonas syringae*;
fire blight (*Erwinia amylovora*);
grey mould (*Botrytis cinerea*);
late blight (*Phytophthora infestans*) in potatoes;
yellow rust (*Septoria* sp., *Stagonospora nodorum*);
fusarium head blight (*Fusarium graminearum*) of wheat and apple scab (*Venturia inaequalis*);
storage diseases of apples (*Penicillium expansum*);
moniliosis (*Monilia fructigena*);
Gloesporioses (*Neofabrea* sp., *Glomerella* sp., *Nectria* sp.).

The invention also relates to a composition for the treatment for protecting a plant tissue, characterized in that it consists of the biologically active substance as defined above or prepared by the process as defined above, obtained in an aqueous medium, in particular at a concentration of 8 to 140 g/L, optionally diluted, optionally concentrated or dehydrated or lyophilized, optionally in combination with at least one of the compatible formulating agents, anti-phytopathogenic agents, in particular selected from the group consisting of fungicidal agents, antibacterial agents, antiviral agents, pesticidal agents and biocontrol agents, plant nutrients, and fruit/vegetable coating agents to form a coating wax.

The invention also relates to a method for the treatment for protecting a plant tissue, characterised in that it consists in applying the composition as defined above, when it is in the aqueous phase, in particular with the biologically active substance after dilution 50 to 400 times, by spraying on the aerial parts of the plants, at the early vegetative stages and/or at the adult and reproductive vegetative stages, in one or more applications, for example up to 40 times, at repeated intervals, in particular every two to thirty days, or by soaking harvested products, such as picked fruits and vegetables, in the said composition in aqueous phase, or by watering roots, or when it is in the form of a coating wax, by coating fruits/vegetables.

The invention also relates to a use characterised by the fact that the biological tissue is human or animal skin, the exogenous agent(s) being oxidising agents, chemical products and/or physical attack agents, and the protective agent is an agent for the cosmetic treatment of the skin, in particular of aged skin with wrinkles to be reduced or of young skin with a suppleness and elasticity to be improved.

The invention also relates to a composition for the protective treatment of human or animal skin, characterised in that it consists of the biologically active substance as defined above or prepared by the process as defined above, in an aqueous medium or in powder form, in combination with at least one cosmetic adjuvant to facilitate its distribution on the skin.

The invention also relates to a process for the treatment for protecting human or animal skin, characterized by the fact that it consists in distributing by spreading or spraying the composition as defined above, in particular in the form of a cream or solution, over the area of skin to be treated in order to obtain a protective effect on the skin at each application, in particular in a proportion of 0.005 to 100 g of biologically active substance per 100 g of composition.

The biological substance of the invention boosts dermal metabolism by increasing the proliferation of fibroblasts and promoting the synthesis of matrix constituents. This activity on the extracellular matrix promotes the elasticity of the skin and the production of collagen. This action contributes to the smoothing of the microrelief of the skin and the reduction of wrinkles.

This reduction in microrelief, together with the activity of stimulating the synthesis of the extracellular matrix, contributes to obtaining the tensor effect observed with the biological substance of the invention.

Moreover, the biological substance of the invention has a protective activity thanks to its antioxidant activity. It allows to restore part of the antioxidant capital and thus to limit the damage caused by free radicals.

Due to its properties on the cell proliferation, the synthesis of extracellular matrix and the protection against free radicals, the biological substance of the invention thus contributes to accelerating this tissue repair process.

DESCRIPTION OF THE PREFERRED EMBODIMENTS

Figure 1:
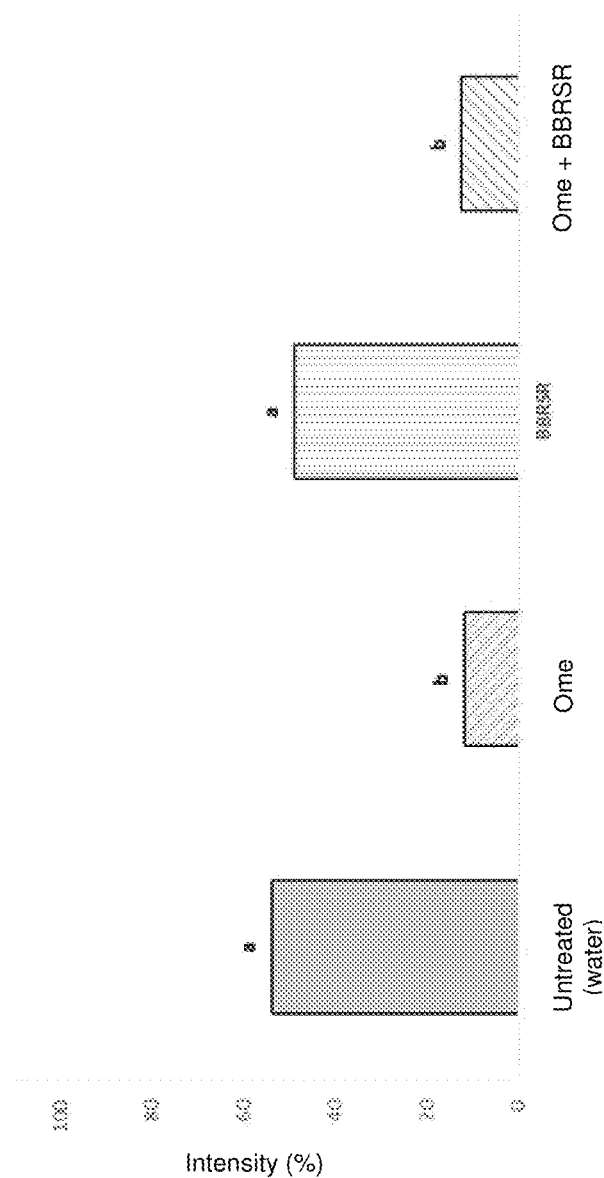
FIG. 1 is a chart illustrating the disease intensity (%) on grapevine bunches attacked by downy mildew after treatment (or not) with oyster mushroom extract, as well as in the Bordeaux mixture programme (oyster mushroom extract/BBRSR)

The following Examples illustrate the present invention without limiting its scope. In these examples, percentages are by weight unless otherwise indicated.

Example 1: Preparation of an Extract of *Pleurotus Ostreatus* in Lyophilized Form The raw material is whole *Pleurotus ostreatus* mushrooms harvested in March. 200 g of dried and crushed *Pleurotus* mushrooms (<10 mm) are dispersed in 2 L of 2% sodium hydroxide in the presence of 0.5% (w/v) sodium borohydride. The extraction was carried out at 50° C. for 8 hours, under mechanical stirring.

The fraction insoluble in NaOH/NaBH$_4$ is removed by filtration at 200 µm. The filtrate obtained is then clarified by successive depth filtrations down to 1 µm.

The clarified extract thus obtained is neutralised by contact with a cation exchange resin (Purolite C150H).

The neutralised extract is clarified by filtration at 1 µm.

A clarified liquid extract is thus obtained, which after lyophilization makes it possible to recover 53 g of a beige powder constituting the extract.

The composition of the extract obtained is reported in Table 1 below

TABLE 1

| Major compounds in the extract | Percentages (% w/w) |
|---|---|
| Total sugars (7) | 45.0 |
| of which neutral oses (1) | 29.2 |
| of which β-glucans (2) | 13.6 |

TABLE 1-continued

| Major compounds in the extract | Percentages (% w/w) |
|---|---|
| of which glucosamine (3) | 2.1 |
| Total protein (4) | 30.1 |
| of which proteins > 3000 Da (5) | 7.8 |
| Mineral matter (6) | 24.9 |
| Mn (kDa) (8) | 25 kDa << 35 kDa for >95% of the organic compounds in the extract |

(1) The amount of neutral oses is obtained by determination by the phenol-sulphuric acid method, according to Dubois et al (Dubois, Gille, Hamilton, Rebers, Smith, Colorimetric method for determination of sugars and relative substances, *Analytical Chemistry* 28, 350-356 (1956)).
(2) The β-glucans are determined by an analysis kit (K-YBGL 09/14, Megazyme).
(3) The quantification of glucosamine is performed by MBTH assay according to Smith et al (Smith & Gilkerson: Quantitation of glycosaminoglycan hexosamine using 3-methyl-2-benzothiazolone hydrazone hydrochloride, *Analytical Biochemistry* 98, 478-480 (1979)).
(4) The amount of total protein is evaluated with a Kjeldahl nitrogen assay and the value obtained is multiplied by 6.25.
(5) Proteins > 3000 Da are determined by the Bradford method (Bradford, A rapid and sensitive method for the quantitation of microgram quantities of protein utilizing the principle of protein-dye binding, *Analytical Biochemistry* 72, 248-254 (1976)).
(6) The mineral matter is quantified following calcination at 650° C.
(7) The amount of total sugars is calculated by difference with the mineral matter and total protein.
(8) The average molecular sizes are determined by steric exclusion chromatography analysis coupled with light scattering and viscometry.

Example 2: Preparation of an Extract of *Pleurotus Ostreatus* in Aqueous Phase

The raw material is whole *Pleurotus ostreatus* mushrooms harvested in May. 200 g of dried and crushed *Pleurotus* mushrooms (<10 mm) are dispersed in 2 L of 2% sodium hydroxide in the presence of 0.5% (w/v) sodium borohydride. The extraction was carried out at 50° C. for 8 hours, under mechanical stirring.

The fraction insoluble in NaOH/NaBH$_4$ is removed by filtration at 200 µm. The filtrate obtained is then clarified by successive depth filtrations down to 1 µm.

The clarified extract thus obtained is neutralised by contact with a cation exchange resin (Purolite C150H). The neutralised extract is clarified by filtration at 1 µm. A clarified liquid extract is obtained containing 34.7 g/L of dry matter constituting the extract.

The composition of the extract obtained is reported in Table 2 below. The composition results are the average of 2 replicates made with the same raw material.

TABLE 2

| Compounds | Percentages |
|---|---|
| Total sugars (7) | 51.8 ± 2.7 |
| of which neutral oses (1) | 27.6 ± 1.3 |
| of which β-glucans (2) | 15.8 ± 2.8 |
| of which glucosamine (3) | 1.6 ± 0.1 |
| Total protein (4) | 22.7 ± 3.6 |
| of which proteins > 3000 Da (5) | 7.1 ± 0.9 |
| Mineral matter (6) | 25.5 ± 0.9 |
| Mn (kDa) (8) | 25 kDa << 35 kDa for >95% of the organic compounds in the extract |

Example 3: Stimulation of the Natural Defences of Tomatoes with the Extract from Example 1

The oyster mushroom extract according to Example 1 was tested on plants to assess the induction of plant defences in the context of pathogen attack after a preventive treatment with the oyster mushroom extract.

The model used is a model of tomato plants grown under glass from seedlings in horticultural potting soil. The plants are one month old at the time of treatment.

They first undergo a pre-treatment consisting of 3 foliar spray applications of the product to be tested. These applications are made at 2-day intervals and until runoff. Then, 7 days after the first application, the pathogen is inoculated in the form of a leaf infiltration of a suspension of *Botrytis cinerea* spores, at a rate of 100,000 conidia per mL of a 0.05% polyethylene sorbitol ester, Tween™ 80, solution. This was a *Botrytis cinerea* strain (reference UBOCC-A-101100) supplied by the Université de Bretagne Occidentale.

Again 7 days later, the plants are harvested, frozen in liquid nitrogen and stored at −20° C. before being analysed.

The peroxidase activity was assessed according to the protocol described by J. S. Shindler, R. E. Childs, and W. G. Bardsley. Peroxidase from Human Cervical Mucus: The Isolation and Characterization. *Eur. J. Biochem.* 65, 325-331 (1976). This enzyme is involved in the regulation of oxidative stress and is classified as a PR protein (Pathogenesis Related protein).

Two products were applied to the plants, namely:

FB: the formulation blank corresponding to a solution known to the person skilled in the art, for example a composition consisting of a surfactant associated with a preservative, which is prepared in distilled water;

Oyster mushroom extract obtained according to Example 1 (35 g dry matter/L) diluted in FB.

Table 3 below shows the peroxidase activities quantified in pre-treated tomato plants:

either by the formulation blank;

or by oyster mushroom extract (Example 1).

Activities are expressed as % of the activity measured for the control (FB formulation blank). Stars correspond to results that are significantly different at the 1% level (Kruskal Wallis test, mean, n=27). The results are the average of 3 independent experiments.

TABLE 3

| Natural defence stimulation activity on tomato | Peroxidase (% activity) |
|---|---|
| Formulation blank | 100 |
| Formulated oyster mushroom extract | 161.9** |

The results shown in Table 3 attest to an effect of oyster mushroom extract on the peroxidase marker of +61.9% compared to the control.

Thus, plants that have been pre-treated with oyster mushroom extract have stimulated defences that enable them to better resist attacks by pathogens.

Example 4: Efficacy of the Oyster Mushroom Extract from Example 2 on Reducing Symptoms of Downy Mildew (*Plasmopara Viticola*) on Grapevines in a Field Trial A field trial was conducted on grapevine (*Vitis vinifera*), Merlot grape variety, during 2018 in the South-West of France, in order to determine the efficacy of the oyster mushroom extract of Example 2 in protection against downy mildew (*Plasmopara viticola*), alone or in a programme with the Bordeaux mixture BBRSR Dispers NC (UPL EUROPE LTD; 750 g Cu/ha). On the experimental plot, 4 microplots per treatment condition were statistically distributed.

The treatments were carried out between 26 Apr. 2018 and 14 Jun. 2018 with a spray volume ranging from 200 to 300 L/ha depending on the increase in leaf area. The untreated control received water sprays; the Bordeaux mixture treatment consisted of applying the equivalent dose of 750 g Cu/ha from flowering (Table 4 below). The oyster mushroom extract obtained according to Example 2 is applied as an aqueous solution formulated with a surfactant and a preservative, the extract is used at a dose of 35 g/ha, either alone or in a programme with Bordeaux mixture. A partial control of Bordeaux mixture alone is also tested to see the contribution of the oyster mushroom extract in such a programme.

Table 4 below shows the treatment schedule for the different modalities.

TABLE 4

| Treatment No. | Treatment | A Dose kg or L/ha | B Dose kg or L/ha | C Dose kg or L/ha | D Dose kg or L/ha | E Dose kg or L/ha | F Dose kg or L/ha | G Dose kg or L/ha | H Dose kg or L/ha |
|---|---|---|---|---|---|---|---|---|---|
| Application stage | | BBCH 14 | BBCH 53 | BBCH 55 | BBCH 57 | BBCH 57 | BBCH 57 | BBCH 65 | BBCH 71 |
| Spray volume | | 200 L/ha | 250 L/ha | 250 L/ha | 300 L/ha | 300 L/ha | 300 L/ha | 300 L/ha | 300 L/ha |
| 1 | Untreated (water) | — | — | — | — | — | — | — | — |
| 2 | Ome | 1 | 1 | 1 | 1 | 1 | 1 | 1 | 1 |
| 3 | BBRSR DISPERSS | | | | | | 3, 75 | 3, 75 | 3, 75 |
| 4 | Ome BBRSR DISPERSS | 1 | 1 | 1 | 1 | 1 | 3, 75 | 3, 75 | 3, 75 |

BBRSR: Bordeaux mixture;
Ome Oyster mushroom extract;
—Water treatment.

[FIG. 1] of the attached drawing shows the disease intensity (%) on grapevine bunches attacked by downy mildew after treatment (or not) with oyster mushroom extract, as well as in the Bordeaux mixture programme (oyster mushroom extract/BBRSR). The ratings shown in FIG. 1 were carried out on 13 June at BBCH 71. The intensity of the attacks is estimated by the surface of the bunches attacked by the disease.

The oyster mushroom extract (Ome) alone allows a reduction of the symptoms of attack by mildew of about 78% compared to the control treated with water. In a program with Bordeaux mixture, the effectiveness of the oyster mushroom extract is 68% compared to the partial control of Bordeaux mixture alone. This Ome/BBRSR program allows to obtain an efficiency of 78% on the reduction of symptoms caused by the mildew of the vine.

Example 5: Efficacy of the Oyster Mushroom Extract from Example 2 on Reducing Symptoms of Downy Mildew (*Plasmopara Viticola*) on Grapevines in a Field Trial A field trial was conducted on grapevine (*Vitis vinifera*), Melon grape variety, during 2018 in North-Western France, to determine the efficacy of the oyster mushroom extract of Example 2 in protection against downy mildew (*Plasmopara viticola*), alone or in a programme with a chemical cover (Table 5 of treatments below). On the experimental plot, 4 microplots per treatment condition were statistically distributed.

The treatments were carried out between 26 Apr. 2018 and 27 Jul. 2018 with a spray volume ranging from 130 to 200 L/ha depending on the increase in leaf area. The untreated control received no spraying; the chemical cover treatment consisted of applying 3 types of conventional products from BBCH 14 stage (Table 5 below). The oyster mushroom extract obtained according to example 2 is applied as an aqueous solution formulated with a surfactant and a preservative, the extract is used at a dose of 35 g/ha, either alone or in a programme with conventional products and in comparison with a complete conventional programme.

Table 5 shows the treatment schedule for the different modalities.

TABLE 5

| Treatment No. | Treatment | A Dose kg or L/ha | B Dose kg or L/ha | C Dose kg or L/ha | D Dose kg or L/ha | E Dose kg or L/ha | F Dose kg or L/ha | G Dose kg or L/ha |
|---|---|---|---|---|---|---|---|---|
| | Application stage | BBCH 14 | BBCH 53 | BBCH 53 | BBCH 55 | BBCH 57 | BBCH 61 | BBCH 65 |
| | Spray volume | 130 L/ha | 130 L/ha | 130 L/ha | 200 L/ha | 200 L/ha | 200 L/ha | 200 L/ha |
| 1 | Control Untreated | | | | | | | |
| 2 | Ome | 1 | 1 | 1 | 1 | 1 | 1 | 1 |
| 3 | LBG 01F34 | | 3 | | 3 | | | |
| | POLYRAM DF | | 2 | | 2 | | | |
| | MIKAL FLASH | | | | | | 4 | |
| | DITHANE NEOTEC | | | | | | | |
| 4 | Ome | 1 | 1 | | 1 | | | |
| | LBG 01F34 | | | | | | | |
| | MIKAL FLASH | | | | | | 4 | |
| | DITHANE NEOTEC | | | | | | | |

| Treatment No. | Treatment | H Dose kg or L/ha | I Dose kg or L/ha | J Dose kg or L/ha | K Dose kg or L/ha | L Dose kg or L/ha | M Dose kg or L/ha | N Dose kg or L/ha |
|---|---|---|---|---|---|---|---|---|
| | Application stage | BBCH 71 | BBCH 73 | BBCH 77 | BBCH 79 | BBCH 79 | BBCH 79 | BBCH 79 |
| | Spray volume | 200 L/ha | 200 L/ha | 200 L/ha | 200 L/ha | 200 L/ha | 200 L/ha | 200 L/ha |
| 1 | Control Untreated | | | | | | | |
| 2 | Ome | 1 | 1 | 1 | 1 | 1 | 1 | |
| 3 | LBG 01F34 | | | | 3 | | 3 | 3 |
| | POLYRAM DF | | | | | | | |
| | MIKAL FLASH | 4 | | | | | | |
| | DITHANE NEOTEC | | | | 2 | | 2 | 2 |

TABLE 5-continued

| 4 | Ome | | | 1 | 1 | 1 |
|---|---|---|---|---|---|---|
| | LBG 01F34 | | 3 | | | |
| | MIKAL | 4 | | | | |
| | FLASH | | | | | |
| | DITHANE | | 2 | | | |
| | NEOTEC | | | | | |

Ome: Oyster mushroom extract (35 g/L);
LBG01F34: Potassium phosphonates (730 g/L);
Polyram DF: Metiram (700 g/kg);
Mikal Flash: Fosetyl/Folpet (500/250 g/kg);
Dithane Neotec: Mancozeb (750 g/kg).

Figure 2:
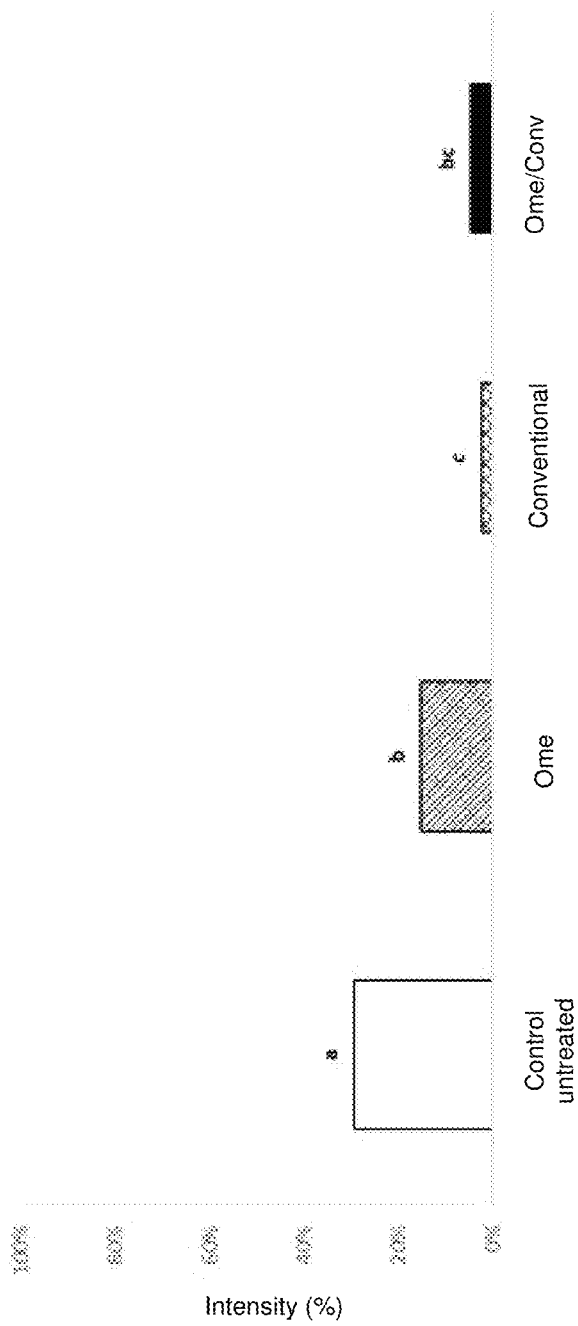
FIG. 2 is a chart illustrating the disease intensity (%) on grapevine bunches attacked by mildew, after treatment (or not) with oyster mushroom extract, as well as in a programme with conventional cover (oyster mushroom extract/Conv)

[FIG. 2] of the attached drawing shows the disease intensity (%) on grapevine bunches attacked by mildew, after treatment (or not) with oyster mushroom extract, as well as in a programme with conventional cover (oyster mushroom extract/Conv). The ratings presented in FIG. 2 were carried out on 24 Jul. 2018 at the BBCH 79 stage. The intensity of the attacks is estimated by the surface of the bunches attacked by the disease.

The oyster mushroom extract (Ome) alone thus allows a reduction of the symptoms of attack by mildew of the order of 48% compared to the untreated control. Replacing 2 applications of 2 chemicals (LBG 01F34 and Polyram DF) with 3 applications of oyster mushroom extract formulated before flowering provides levels of protection statistically equivalent to total conventional coverage (Conventional). This Ome/Conv programme is 84% effective in reducing symptoms caused by mildew on vines.

Example 6: Efficacy of Oyster Mushroom Extract from Example 2 on Reducing Septoriosis (*Septoria Tritici*) Symptoms in Wheat in a Field Trial A field trial was conducted on common wheat (*Triticum aestivum*), an Advisor variety during 2018 in the North-West of France, to determine the efficacy of the oyster mushroom extract of Example 2 in protection against the septoriosis in soft wheat (*Septoria tritici*), alone or in a programme with a chemical cover (see Table 6 of treatments). On the experimental plot, 5 microplots per treatment condition were statistically distributed.

The treatments were carried out between 22 Mar. 2018 and 3 May 2018 with a spray volume of 200 L/ha. The untreated control is sprayed with water; the chemical cover treatment consists of applying 2 types of conventional products from the BBCH 29 stage (Table 6). The oyster mushroom extract obtained according to Example 2 is applied as an aqueous solution formulated with a surfactant and a preservative, the extract is used at a dose of 35 g/ha, either alone or in a programme with conventional products and in comparison with a complete conventional programme.

Table 6 below shows the treatment schedule for the different modalities.

TABLE 6

| Trt No. | Treatment | T0 Dose kg or L/ha | T1 Dose kg or L/ha | T2 Dose kg or L/ha |
|---|---|---|---|---|
| Application stage | | 29 | 32 | 39 |
| Spray volume | | 200 L/ha | 200 L/ha | 200 L/ha |

TABLE 6-continued

| Trt No. | Treatment | T0 Dose kg or L/ha | T1 Dose kg or L/ha | T2 Dose kg or L/ha |
|---|---|---|---|---|
| 1 | Untreated (water) | — | — | — |
| 2 | CHEROKEE | | 2 | |
| | ADEXAR | | | 2 |
| 3 | COV17-01 | 1 | 1 | 1 |
| 4 | COV17-01 | 1 | 1 | |
| | ADEXAR | | | 2 |

Ome: Oyster mushroom extract (35 g/L) formulated;
CHEROKEE: Propiconazole/Cyproconazole/Chlorothalonil (62.5/50/375 g/L);
ADEXAR: Epoxiconazole/Fluxapyroxad (62.5/62.5 g/L);
— Water treatment.

Figure 3:
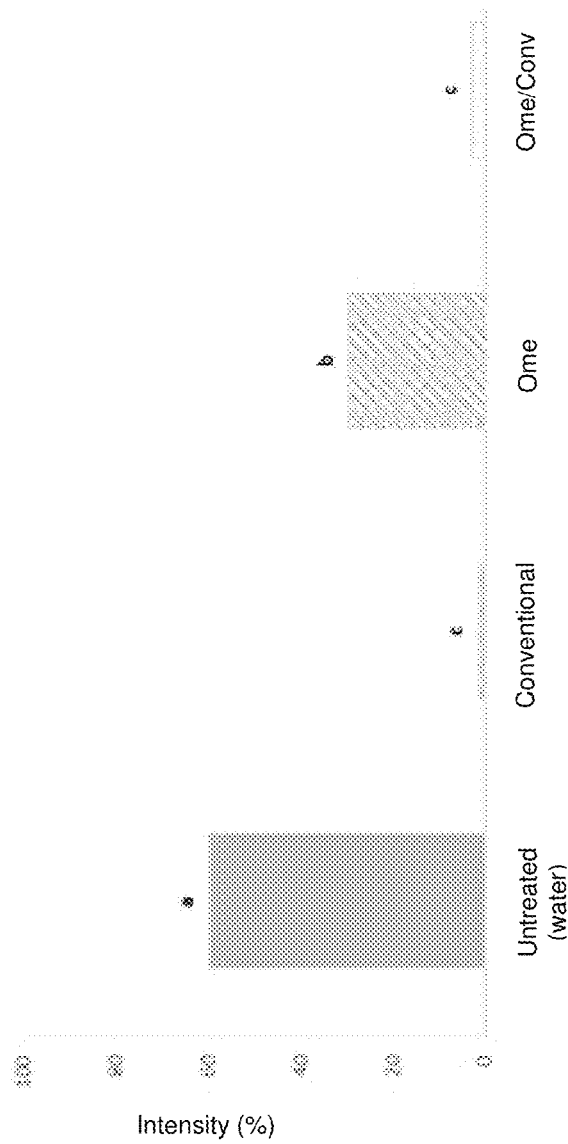
FIG. 3 is a chart illustrating the disease intensity (%) on the F1 leaf of soft wheat attacked by septoriosis after treatment (or not) with oyster mushroom extract, as well as in a programme with conventional cover (Ome/Conv).

[FIG. 3] of the attached drawing shows the disease intensity (%) on the F1 leaf of soft wheat attacked by septoriosis after treatment (or not) with oyster mushroom extract, as well as in a programme with conventional cover (Ome/Conv). The ratings presented in FIG. 3 were carried out on 18 Jun. 2018 at the BBCH 75 stage. The intensity of the attacks is estimated by the surface of the leaves attacked by the disease.

The oyster mushroom extract (Ome) alone therefore allows a reduction in septoriosis symptoms of the order of 50% compared to the water treated control. Replacing one chemical application (Cherokee) with two applications of formulated oyster mushroom extract provides protection levels that are statistically equivalent to total conventional coverage (Conventional). This Ome/Conv programme achieves 95.5% efficacy in reducing symptoms caused by septoriosis in wheat.

Example 7: Antioxidant Activity of Extracts from Examples 1 and 2

Principle:

The evaluation of the antioxidant activity was carried out by the ORAC (Oxygen Radical Antioxidant Capacity) method. It consists of measuring the protection exerted by a given molecule against the oxidation of fluorescein (CAS 518-47-8) by a stable free radical, AAPH (2,2'-azobis(2-amidino-propane)dihydrochloride) (CAS 2997-92-4).

The results, reported in Table 7 below, are expressed in relation to the protection provided by a reference antioxidant, Trolox (CAS 53188-07-1).
Standard range: 0.002M Trolox stock solution (25 mg in 50 ml phosphate buffer).
Dilution of samples: performed in phosphate buffer at pH 7.4.

TABLE 7

| Species | Activity in μmol Trolox equivalent/g |
|---|---|
| Extract according to example 1 | 179 ± 9 |
| Extract according to example 2 | 144 ± 7 |

It can be seen that the production of the extract according to the invention makes it possible to obtain an anti-oxidant activity.

Example 8: Evaluation of the Impact of the Extract from Example 1 on Fibroblast Proliferation The objective is to evaluate the impact of the oyster mushroom extract obtained according to Example 1 on tissue repair in the skin. This evaluation is done in comparison with an untreated control.

The dry oyster mushroom extract obtained in Example 1 is diluted in DMEM Glutamax culture medium to obtain a 1 mg/mL stock treatment solution which is then filtered at 0.2 μm to remove any microorganism contamination.

The operating protocol is as follows:

Primary cultures of 44-year-old human skin fibroblasts (PAF 08052) are seeded in 48-well microplates at 10,000 cells per well with a culture medium volume (DMEM glutamax) of 500 μL. The cells adhere to the bottom of the wells for 24 hours. The culture medium is then replaced by the extract obtained according to Example 1, diluted in culture medium and then filtered, and a control without treatment will be performed (DMEM glutamax). Several concentrations will be tested at 500 μL per well and incubated for 48 hours at 37° C. in an atmosphere containing 5% $CO_2$ by volume. The cells are then detached with trypsin and counted on a Malassez slide. The analyses were performed on 6 replicates.

The results, shown in Table 8 below, are expressed as percentages of proliferation compared to the untreated control. A statistical analysis by Wilcoxon-Mann-Withney test is performed on the results to determine the significance of the values. Significance stars indicate the degree of significance i.e. *p<0.05; ***p<0.001.

TABLE 8

| Concentration of the extract | Proliferation percentage |
|---|---|
| Untreated control | 100.0 |
| 50 μg/mL | 133.5 *** |
| 200 μg/mL | 127.5 * |
| 250 μg/mL | 161.9 *** |
| 450 μg/mL | 125.0 * |
| 650 μg/mL | 133.3 * |
| 750 μg/mL | 133.3 * |
| 900 μg/mL | 137.5 * |

The extract obtained according to Example 1 was found to promote fibroblast proliferation significantly compared to the untreated control, and thus tissue repair with better activity at 250 μg/mL.

Example 9: Evaluation of the Impact of the Extract from Example 1 on Keratinocyte Proliferation The objective is to evaluate the impact of the oyster mushroom extract obtained according to Example 1 on epidermal repair. This evaluation is done in comparison with an untreated control.

The oyster mushroom extract according to Example 1 is diluted in KGM Gold culture medium to obtain a 1 mg/mL stock treatment solution which is then filtered at 0.2 μm to remove any contamination by micro-organisms.

The operating protocol is as follows:

Primary cultures of 43-year-old human skin keratinocytes (NHEK 33228) are seeded in 48-well microplates at 10,000 cells per well with a volume of 500 μL KGM Gold culture medium. The cells adhere to the bottom of the wells for 48 hours. The culture medium is then replaced by the extract obtained according to Example 1 diluted in culture medium and filtered; in addition, a control without treatment (only culture medium) will be carried out. Several concentrations will be tested at a rate of 500 μL per well and incubated for 48 hours at 37° C. in an atmosphere enriched with 5% $CO_2$ by volume. The tests are performed in triplicates. The cells are then detached with Trypsin-EDTA and counted on a Malassez slide.

The results, shown in Table 9 below, are expressed as percentages of the untreated control. A statistical analysis by Wilcoxon-Mann-Withney test is performed on the results to determine the significance of the values. Significance stars indicate the degree of significance i.e. *p<0.05; **p<0.01.

TABLE 9

| Concentration of the extract | Proliferation percentage |
|---|---|
| Untreated control | 100.0 |
| 50 μg/mL | 90.0 |
| 100 μg/mL | 140.0 * |
| 300 μg/mL | 150.0 ** |
| 750 μg/mL | 160.0 * |

The extract according to Example 1 was found to promote keratinocyte proliferation significantly compared to the untreated control from 100 μg/mL with a higher activity at 750 μg/mL.

Example 10: Comparison of Peroxidase Activity on Tomato after Treatment with the Extract According to Patent WO 2018/069497 and Example 1

This study shows the stimulation of tomato defences by the different oyster mushroom extracts in the presence of *Botrytis cinerea:*

The first extract (Extract B1) corresponds to the extract obtained according to patent WO 2018/069497 from *Pleurotus ostreatus.*

The second extract (Extract B2) is obtained according to the process described in Example 1 from *Pleurotus ostreatus.*

The 2 extracts are tested in the same trial in comparison with the co-formulants alone (Formulation blank) and a control containing only distilled water (DW).

The model used is a model of Marmande tomato plants grown under glass from seedlings in horticultural potting soil. The plants are one month old at the time of treatment.

At t=0, the plants are treated by foliar spraying with the test product (1 spray to runoff of an aqueous solution). The operation is repeated at t=2 days and t=5 days. The controls are treated with the formulation blank or distilled water.

At t=7 days after the first application, the pathogen was inoculated in the form of a leaf infiltration of a suspension of *Botrytis cinerea* spores at a rate of 100,000 conidia per mL of a 0.05% polyethylene sorbitol ester, Tween™ 80, solution. This was a *Botrytis cinerea* strain (reference UBOCC-A-101100) supplied by the Université de Bretagne Occidentale.

At t=14 days, treated leaves, which differ from inoculated leaves, were harvested by taking leaf discs from each plant, which were frozen in liquid nitrogen and stored at −20° C. before being analysed.

The peroxidase activity was assessed according to the protocol described by J. S. Shindler, R. E. Childs, and W. G. Bardsley. Peroxidase from Human Cervical Mucus: The Isolation and Characterization. Eur. J. Biochem. 65, 325-331 (1976). This enzyme is involved in the regulation of oxidative stress and is classified as a PR protein (Pathogenesis Related protein).

The specific enzyme activities are expressed as % of the activity measured for the control (distilled water DW).

The Table 10 shows the peroxidase activity extracted from tomato plants treated by 3 sprays with:
Oyster mushroom extract 1 (35 g dry matter/L) diluted in FB,
Oyster mushroom extract 2 (35 g dry matter/L) diluted in FB,
distilled water (control)
the formulation blank
then inoculated with *Botrytis cinerea*.

TABLE 10

| Treatment | Peroxidase activity (% of DW control) |
| --- | --- |
| Distilled water | 100 ± 22.76 |
| Formulation blank | 118 ± 21.02 |
| Oyster mushroom extract 1 | 132 ± 25.90 |
| Oyster mushroom extract 2 | 195 ± 25.07 |

The treatment with the formulation blank did not induce a significant increase in peroxidase activity in tomato plants under these treatment conditions. The same was true for oyster mushroom extract 1, although the average activity was higher than that of the control and the formulation blank. On the other hand, a strong stimulation of the peroxidase enzymatic activity is observed following the pre-treatment of tomato plants with oyster mushroom extract 2; the increase in activity compared to the control is significant (×1.9) according to the Kruskal Wallis statistical test, as well as compared to the treatment with extract 1 (×1.48)

The invention claimed is:

1. A biologically active substance obtained by:
    alkaline extraction, using an aqueous solution of at least one base in the presence of at least one reducing agent, of at least one macroscopic edible mushroom reduced to powder, to obtain a mixture having a liquid portion containing the soluble extracted materials and a solid portion formed of insoluble solid particles;
    filtering the resulting mixture to remove the solid portion;
    neutralising the liquid portion using at least one strong acid cation exchange resin in a manner configured to remove excess cations introduced during the alkaline extraction step, effectively neutralizing the liquid portion wherein the cation exchange resin is selected from resins having sulphonic, phosphorus, carboxymethyl or carboxylic groups; and
    treating the resulting aqueous phase, the treatment being selected from dilution in water, concentration, dehydration and lyophilisation, to obtain a biologically active substance which is, respectively, more diluted in water, in an aqueous solution that is more concentrated, dehydrated in powder form or lyophilised,
    said biologically active substance comprising, per 100 parts by weight of dry matter:
        30 to 75 parts by weight of total sugars, of which:
            9 to 25 parts by weight of ß-glucans; and
            0.8 to 2.4 parts by weight of glucosamine and/or acetylated glucosamine;
        7 to 36 parts by weight of total peptides/total proteins;
            the remainder being mineral matter,
        80 to 100% of the organic compounds having a mass, based on the average molecular size, of between 20 and 45 kDa.

2. The biologically active substance according to claim 1, wherein the mushroom or mushrooms subjected to the extraction is (are) selected from the group formed by oyster mushrooms, parasol mushrooms and button mushrooms.

3. The biologically active substance according to claim 1, wherein the base is selected from sodium hydroxide and potassium hydroxide; and the reducing agent(s) is (are) selected from alkali borohydrides.

4. A method for protecting a biological tissue against attack by at least one exogenous agent, comprising providing the biologically active substance of claim 1, and applying an effective amount of the biologically active substance to the biological tissue.

5. The method according to claim 4, wherein the biological tissue is a plant tissue, and the exogenous agent is pathogenic fungi, bacteria, viruses, insects, or environmental stresses selected from the group consisting of rain, frost, and temperature.

6. A composition for the treatment for protecting a plant tissue, comprising the biologically active substance as defined in claim 1, obtained in an aqueous medium.

7. A process for the treatment for protecting a plant tissue, comprising applying the composition as defined in claim 6, when the composition is in the aqueous phase, by spraying on the aerial parts of the plants, at the early vegetative stages and/or at the adult and reproductive vegetative stages, in one or more applications, or by soaking the harvested products, in the composition in aqueous phase, or by watering roots, or when the composition is in the form of a coating wax, by coating fruits/vegetables.

8. The method according to claim 4, wherein the biological tissue is human or animal skin, and the exogenous agent is an oxidizing agents or a chemical products.

9. A protective treatment composition for human or animal skin, comprising the biologically active substance as defined in claim 1, in an aqueous medium or in powder form, in combination with at least one cosmetic adjuvant to facilitate distribution of the protective treatment composition on the skin.

10. A process for the treatment for protecting human or animal skin, comprising distributing by spreading or spraying the composition as defined in claim 9, in over the area of skin to be treated in order to obtain a protective effect on the skin at each application.

11. The composition of claim 6, wherein the biologically active substance is present in the aqueous medium at a concentration of 8 to 140 g/L.

12. The biologically active substance according to claim 2, wherein the base is selected from hydroxylated bases; and the reducing agent(s) is (are) selected from alkali borohydrides.

* * * * *